United States Patent
Lindsay

(10) Patent No.: US 9,633,168 B2
(45) Date of Patent: Apr. 25, 2017

(54) BIOMETRIC IDENTITY VALIDATION FOR USE WITH UNATTENDED TESTS FOR MEDICAL CONDITIONS

(75) Inventor: Noel Lindsay, Ross, CA (US)

(73) Assignee: Sleep Science Partners, Inc., Larkspur, CA (US)

(*) Notice: Subject to any disclaimer, the term of this patent is extended or adjusted under 35 U.S.C. 154(b) by 518 days.

(21) Appl. No.: 13/087,254

(22) Filed: Apr. 14, 2011

(65) Prior Publication Data

US 2011/0254662 A1  Oct. 20, 2011

Related U.S. Application Data

(60) Provisional application No. 61/324,195, filed on Apr. 14, 2010.

(51) Int. Cl.
*G05B 19/00* (2006.01)
*G06F 19/00* (2011.01)

(52) U.S. Cl.
CPC .................. *G06F 19/322* (2013.01)

(58) Field of Classification Search
CPC ........................................................ G06F 21/32
USPC .... 340/539.13, 539.12, 5.6, 573.1; 378/165; 382/116, 115; 600/301, 300; 713/176; 1/1
See application file for complete search history.

(56) References Cited

U.S. PATENT DOCUMENTS

| | | | | |
|---|---|---|---|---|
| 4,617,525 A * | 10/1986 | Lloyd | ................. | A61M 21/02 128/204.23 |
| 6,641,532 B2 * | 11/2003 | Iliff | ............................. | 600/300 |
| 7,428,554 B1 * | 9/2008 | Coberley | ................ | G06F 19/28 |
| 8,150,108 B2 * | 4/2012 | Miller | ................ | G06K 9/00892 340/5.53 |
| 2002/0186818 A1 * | 12/2002 | Arnaud | ................. | A61B 6/583 378/165 |
| 2003/0135097 A1 * | 7/2003 | Wiederhold | ....... | A61B 5/02055 600/301 |
| 2004/0003295 A1 * | 1/2004 | Elderfield | .......... | G07C 9/00087 713/176 |
| 2004/0025030 A1 * | 2/2004 | Corbett-Clark | ....... | G06F 19/322 713/186 |
| 2004/0236189 A1 * | 11/2004 | Hawthorne | ......... | G06F 19/3412 600/300 |
| 2005/0068169 A1 * | 3/2005 | Copley | .............. | G08B 21/0283 340/539.13 |
| 2008/0212847 A1 * | 9/2008 | Davies et al. | ................ | 382/115 |

(Continued)

*Primary Examiner* — Andrew Bee
*Assistant Examiner* — Israel Daramola
(74) *Attorney, Agent, or Firm* — Carr & Farrell LLP

(57) ABSTRACT

An initial signature may be generated from an initial set of biometric data. A subsequent set of biometric data may be received along with diagnostic data, and a subsequent signature may be generated from the subsequent set of biometric data. The initial signature and the subsequent signature maybe compared to determine if there is an acceptable degree of matching between the signatures. If the signatures match, such as for example within a threshold percentage, the second set of biometric data is determined to be from the same a subject as the initial set of biometric data, and the diagnostic data is processed for that subject. If the signatures do not match, the initial and subsequent sets of biometric data are determined to be from different people and the diagnostic data is not processed.

13 Claims, 5 Drawing Sheets

(56) References Cited

U.S. PATENT DOCUMENTS

| | | | | |
|---|---|---|---|---|
| 2009/0005652 A1* | 1/2009 | Kurtz | ............... | A61B 5/00 |
| | | | | 600/300 |
| 2010/0114993 A1* | 5/2010 | Holschbach | ......... | G06F 19/322 |
| | | | | 707/810 |
| 2010/0253505 A1* | 10/2010 | Chou | ............... | A61B 5/0404 |
| | | | | 340/539.12 |
| 2011/0001605 A1* | 1/2011 | Kiani | ............... | G06F 19/327 |
| | | | | 340/5.6 |

* cited by examiner

BIOMETRIC IDENTITY VALIDATION FOR USE WITH UNATTENDED TESTS FOR MEDICAL CONDITIONS

CROSS-REFERENCE TO RELATED APPLICATION

This application claims the priority benefit of U.S. Patent Application Ser. No. 61/324,195, filed Apr. 14, 2010, and entitled "BIOMETRIC IDENTITY VALIDATION FOR USE WITH UNATTENDED TESTS FOR MEDICAL CONDITIONS," the disclosure of which is incorporated herein by reference.

BACKGROUND

Sleep apnea is a condition which may affect the ability of professionals to perform their job. It would be desirable for companies and government agencies to be able to determine whether current and prospective employees may have sleep apnea in order to take necessary precautions while those employees perform their work.

Historically, sleep apnea has been diagnosed using an overnight sleep study in a purpose-specific facility which is attended by sleep technicians. However new technology and developments in the field of practice now allow ambulatory sleep monitors to be used to do sleep testing in the home. Without the oversight of sleep technicians who would normally confirm that the sleep apnea monitoring system was actually monitoring the intended subject, it can be difficult to confirm if the ambulatory sleep monitor is used by the intended subject or someone else in place of the subject. Put another way, it could be difficult to detect if a subject fraudulently allowed another person to be monitored rather than the intended subject.

SUMMARY OF THE INVENTION

The present technology may provide a system that validates the identification of a subject who is being tested to determine the presence or absence of a medical condition, such as for example sleep apnea, without being monitored by attending personnel. A first set of biometric data associated with a subject may be received by a system from a biometric monitor at a time when and at a place where the subject's identity may be validated, thereby creating an initial biometric signature. A subsequent set of biometric data may be received along with diagnostic data, such as the results of a home sleep test to determine the presence or absence of sleep apnea. This subsequent set of biometric data would be used to create a subsequent biometric signature. The initial signature and the subsequent signature may then be compared to determine if there is an acceptable match. If the signatures match well enough, for example based on some pre-specified set of criteria or a threshold, the second set of biometric data is determined to have been obtained from the same a subject as the initial set of biometric data, and the diagnostic data is validated for that subject. If the signatures do not match, the initial and subsequent sets of biometric data are determined to be from different people and the diagnostic data is not processed. In this manner, diagnostic data such as the results of a home sleep test used to determine the presence or absence of sleep apnea can be validated to correspond to a particular subject, even though the data is collected without supervision while the subject is sleeping.

In an embodiment, a method for validating diagnostic data associated with a subject may include receiving biometric data and diagnostic data for a subject. The biometric data and diagnostic data may be associated with a diagnostic session, and the biometric data may be received from a monitoring device. A biometric signature may be generated from the received biometric data. The diagnostic data associated with the biometric signature may be validated if the biometric signature is determined to match an initial biometric signature associated with the subject.

In an embodiment, a system for validating diagnostic data may include a communications module, a signature generation module, and a signature comparison module, all of which may be stored in memory and executed by a processor. The communications module may receive biometric data collected from a biometric monitor. The signature generation module may generate an initial biometric signature from the received biometric data. The signature comparison module may compare the initial biometric signature and a subsequent biometric signature to determine if the signatures are associated with the same subject.

DETAILED DESCRIPTION

Figure 1:
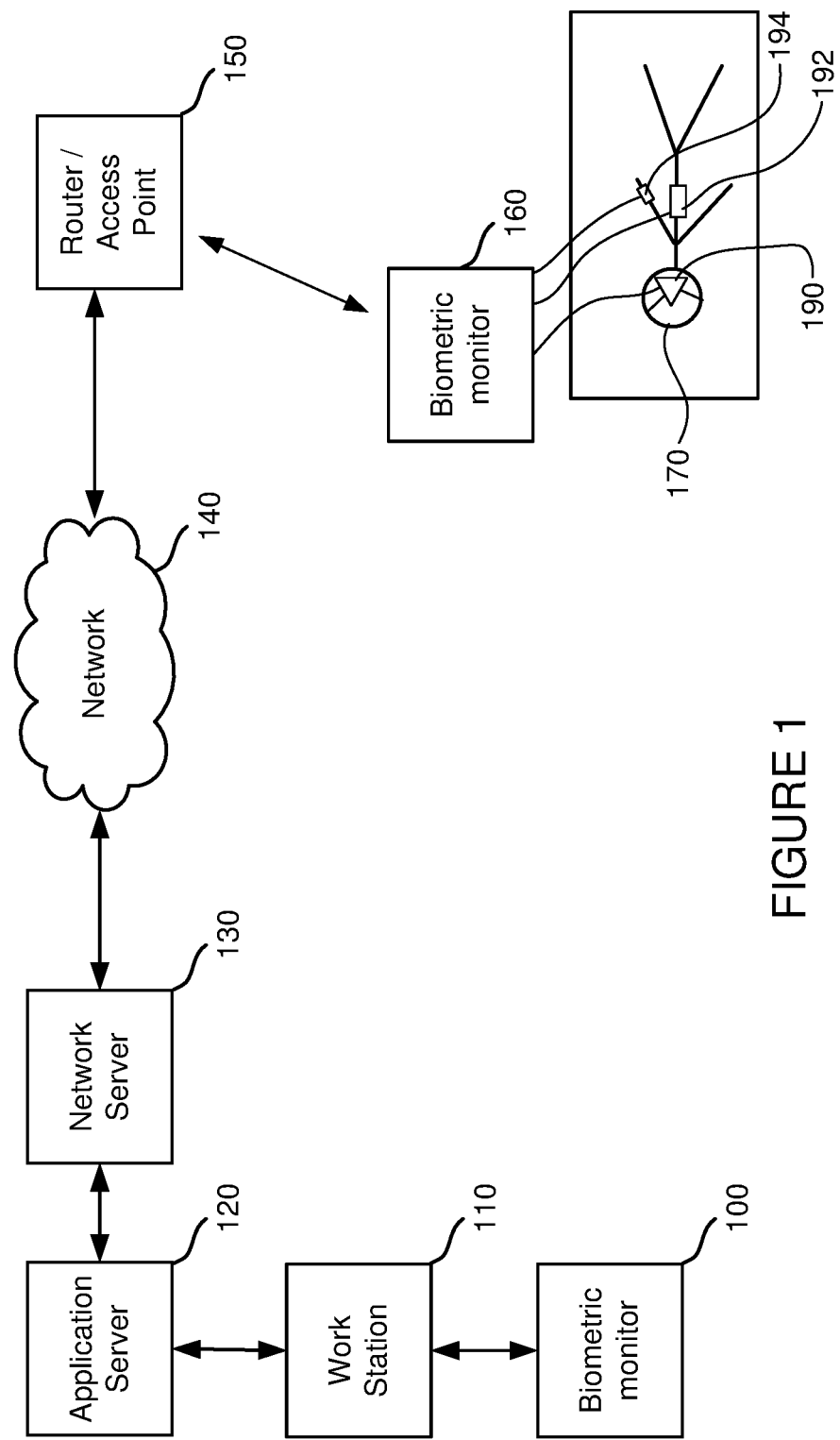
FIG. 1 is a block diagram of an exemplary environment for validating subject biometric data.

The present technology may provide a system that validates the identity of a subject who is being tested to determine the presence or absence of a medical condition. A first set of biometric data associated with a subject may be received by a system from a biometric monitor at a time when and at a place where the subject's identity may be validated, thereby creating an initial biometric signature. A subsequent set of biometric data may be received along with subsequent diagnostic data, and a subsequent signature may be generated from the subsequent set of biometric data. The initial signature and the subsequent signature may then be compared to determine if there is an acceptable degree of matching between the signatures. If the signatures match well enough, for example within an overall threshold of ninety percent (90%), an overall percentage greater than fifty percent (50%), or based on some other pre-specified set of criteria, the second set of biometric data is determined to be from the same a subject as the initial set of biometric data, and the diagnostic data is processed for that subject. If the signatures do not match, the initial and subsequent sets of biometric data are determined to be from different people and the diagnostic data may not validated or processed. In this manner, diagnostic data such as the results of a home sleep test used to determine the presence or absence of sleep apnea data can be validated to correspond to a particular subject, even though the data is collected without supervision while the subject is sleeping.

The present technology may be used in several applications. For example, the present monitoring and validating system may be used with an ambulatory sleep monitor or home sleep monitor. Ambulatory sleep monitors are used to monitor a subject's sleep at home, or other location besides a monitoring facility, to detect sleep disorders such as sleep apnea. Examples of areas of employment in which a diagnosis of sleep apnea may impact public safety include truck drivers and constructions workers. Because the ambulatory sleep monitor device is used to help diagnose conditions that may affect the performance or safety of a subject while performing their job, it is important that the data obtained is actually for the intended subject. The present technology may be used to validate that data received from an ambulatory sleep monitor is actually associated with the intended subject.

Another application of the present technology is for monitoring and validating use of devices that measure various electrical activity of the central nervous system, such as a Holter monitor. A Holter monitor may be used for monitoring heart activity via electrocardiography (ECG) or electroencephalography (EEG) over a period of time. The present technology may be used to validate that a subject using a Holter monitor is an intended subject of the device.

The biometric monitor of the present technology is designed to prevent the gathering of diagnostic data from a source other than an intended subject. To validate that diagnostic data is obtained from an intended subject, one or more biometric signatures are generated from data obtained from the individual providing the diagnostic data. The biometric signatures may be generated from any of several medical monitoring machines, including ECG, pulse-oximetry, or other devices. Additionally, a monitored individual may be fitted with an identification (ID) device that can detect if it is removed or tampered with. For example, a wrist band with both an identification mechanism and an anti-tampering mechanism may be worn by the monitored individual during monitoring. The identification mechanism may be an RFID device or other means for communicating with a monitoring mechanism. The anti-tampering mechanism may prevent the wrist band from being removed from an individual without damaging the wrist band, or affecting the identification mechanism. In some embodiments, the validation of the subject's biometric signature may include confirming the presence and integrity of the identification device. Confirming the presence of the ID device may include detecting the proximity of the device via RFID. Confirming the integrity of the ID device may include detecting that the ID device has not been removed, stretched, or otherwise tampered with.

FIG. 1 is a block diagram of an exemplary environment for validating subject biometric data. The environment of FIG. 1 includes biometric monitors 100 and 160, work station 110, application server 120, network server 130, network 140, router/access point 150, and subject 170.

Work station 110 may be used to receive and process diagnostic data and biometric data. The work station may include one or more modules stored in memory of the work station and executable by a processor. The modules may include a communications module, a signature generation module, and a signature comparison module. The communications module may communicate with one or more biometric monitors, either directly or via one or more devices and networks (e.g., via one or more servers and the Internet). The signature generation module may generate one or more biometric signatures from biometric data received by the communications module. The signature comparison module may compare one or more signatures generated by the signature generation module to determine if they signatures match within a particular threshold. The diagnostic data may include data obtained by a medical monitoring device for identifying the presence or absence of a medical condition in the subject. Examples of diagnostic data include sleep apnea data and Holter monitor data.

Biometric data may include data collected by a biometric monitor and is used to generate a biomedical signature for the subject. Examples of biometric data include ECG data, pulse oximetry data, and other data. The diagnostic data and biometric data may be provided to work station 110 by a biometric monitor 100 or 160 or some other subject monitoring or data capturing device (not illustrated in FIG. 1).

Work station 110 may communicate with a biometric monitor 100 through a direct connection. Work station 110 may also communicate with a remote biometric monitor 160 over a network 140. Work station 110 may receive diagnostic data and determine whether a subject associated with the data has a particular medical condition such as sleep apnea. Work station 110 may also receive and process biometric data, for example to identify a biometric signature for the subject. The biometric signature may be based on electrocardiogram (ECG) data. For example, an ECG may be taken for a subject over a period of time, for example 5 minutes. A biometric signature or identifier may include data that describes a pattern in the ECG associated with the subject. Work station 110 may generate a plurality of biometric signatures, including an initial and subsequent signature, from one or more sets of biometric data. The work station 110 may compare an initial biometric signature and subsequent biometric signature to determine if there is a satisfactory level of matching between the two signatures, indicating whether the two signatures were likely to be from the same person.

Application server 120 communicates with work station 110 and may perform all or a portion of the processing discussed above with respect to work station 110. Application server 120 may receive data, including biometric data and diagnostic data, from a remote biometric monitor through network server 130, network 140, and router/access point 150.

Network 140 can include any type of data communication network, including an intranet, the Internet, a LAN, WAN, public network, private network, and any combination of these. Network server 130 communicates with network 140 and provides communications to and from application server 120. When network 140 is the Internet, network server 130 may function as a web server.

Router/Access Point 150 may communicate with network 140 and biometric monitor 160. For example, biometric data and diagnostic data may be communicated between the network (such as the Internet) and biometric monitor 160.

Biometric monitor 160 may be in communication with one or more sensors attached to a subject 170. For example, biometric monitor 160 may be attached to an airflow sensor 190 positioned near the subject's mouth and/or nose, one or more ECG electrodes 192 positioned on the subject's chest, and a pulse oximetry sensor 194 typically positioned on one of the subject's fingers. The data from these sensors and electrodes may be captured and communicated to biometric monitor 160. Biometric monitor 160 may then store the data until the biometric monitor 160 is connected to work station 110. Biometric monitor 160 may also transmit the data to work station 110 via network 140 using router/access point 150, network server 130, and application server 120.

In some embodiments, biometric data collected by biometric monitor 160 to work station 110 may be stored and transmitted to work station 110 at a later time. The biometric data may also be transmitted to work station 110 and processed at a later time by a user of the work station, or automatically by the work station. In an embodiment, the biometric data may be transmitted over an established connection with the work station 110 while the biometric data is collected and analyzed by the work station as the data is received. This real time processing of the biometric data may be performed with or without a user at the work station 110.

Figure 2:
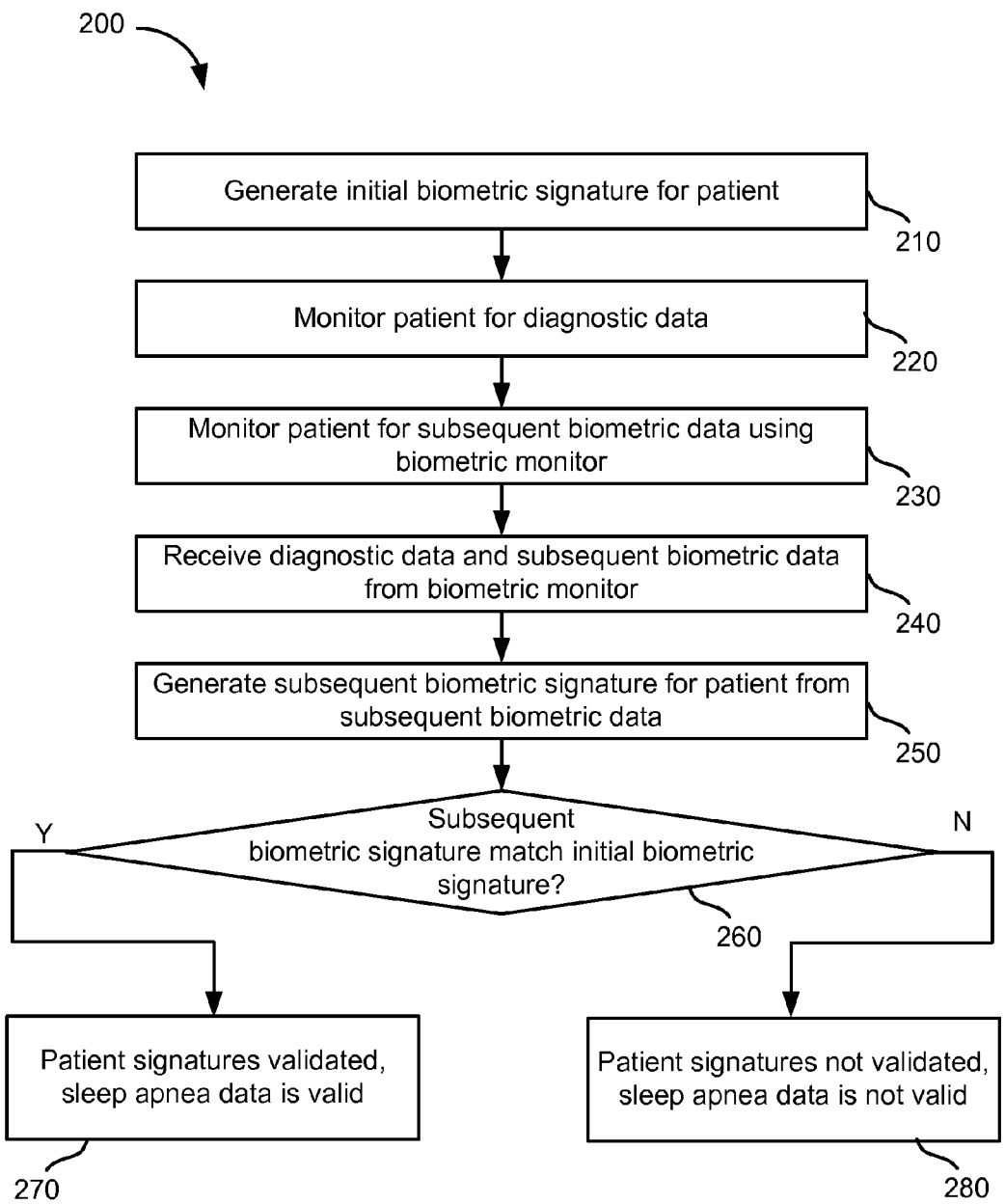
FIG. 2 is a flow chart of an exemplary method for validating subject biometric data.

FIG. 2 is a flow chart of an exemplary method for validating subject biometric data.

An initial biometric signature may be generated for a subject at step 210. The initial biometric signature may be generated using a biometric monitor 100 in communication with a work station 110. The biometric monitor 100 may collect data from a subject for the initial biometric signature at a monitoring facility, such as a medical clinic, hospital, or other location. Once the data initial biometric signature is generated, the signature is stored for comparison to a subsequently obtained signature. Generating an initial biometric signature is discussed in more detail below with respect to the method of FIG. 3.

Diagnostic data may be gathered by monitoring a subject using a biometric monitor 160 at step 220. In some embodiments, the biometric monitor device may include both ECG electrodes and other sensors used to perform a home sleep test to determine the presence or absence of sleep apnea. The biometric monitor 160 may include multiple devices, wherein at least one device is suitable for gathering diagnostic data (which may or may not include sleep apnea data) and at least one device is suitable for gathering biometric data from the subject.

The subject may be monitored for subsequent biometric data using the biometric monitor 160 or other device at step 230. The biometric data monitoring at step 230 may be the same type of monitoring, or capture similar data, as the monitoring performed at step 200. However, the subsequent monitoring at step 230 is performed outside a monitoring facility and is used to generate data suitable for comparison purposes. Monitoring a subject for diagnostic data using a biometric monitor at step 220 and monitoring a subject for subsequent biometric data at step 230 may be performed in a manner, such as for example by the biometric monitor 160 simultaneously, that prevents the subject from circumventing the process or providing diagnostic data and biometric data by the same person.

Diagnostic data and the subsequent biometric data may be received from biometric monitor 160 at step 240. The data may be received by work station 110 (or application server 120) at step 240 over network 140 or via a direct communication to work station 110. When received through direct connection, the biometric monitor may be brought to the proximity of work station 110 (or application server 120) and the data captured by the biometric monitor may be communicated from biometric monitor 160 to work station 110 (or application server 120) via a direct data link.

A subsequent biometric signature for the subject is generated from the subsequent biometric data at step 250. The signature may be generated from the received biometric data in the same fashion that the initial biometric signature is generated with respect to step 210.

A determination is made as to whether the subsequent biometric signature matches the initial biometric signature at step 260. The initial biometric signature and subsequent biometric signature are generated using the same method from the corresponding received biometric data, such as for example an ECG, fingerprint scan, voice recognition, or some other form of biometric identification. When the biometric data for the initial and subsequent biometric signature is generated using the same method and for the same person, the resulting signatures should match within a certain degree, such as for example ninety percent, ninety-five percent, or some other threshold that may be determined based on the system used and the methodology used to quantify the biometric signature. Determining whether an initial biometric signature and a subsequent biometric signature match is discussed in more detail below with respect to the method of FIG. 4.

If the subsequent biometric signature is determined to be a match with the initial biometric signature at step 260, such as for example within a particular threshold, the signatures are determined to be from the same subject and the diagnostic data received from the subject is validated at step 270. If the subsequent biometric signature and initial biometric signature do not match (within a threshold, if any), the signatures may be from different subjects and the diagnostic data received with the subsequent biometric data is not processed in step 280.

Figure 3:
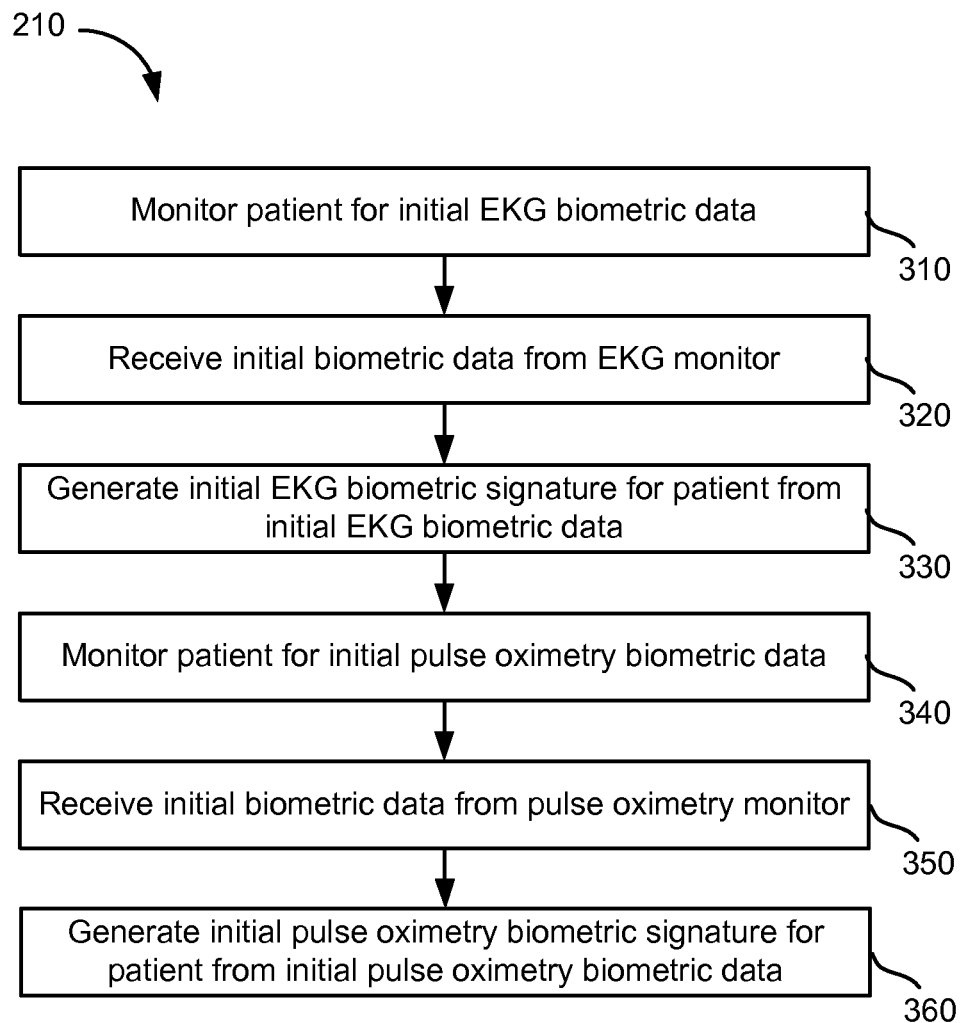
FIG. 3 is a flow chart of an exemplary method for generating initial biometric signatures.

FIG. 3 is a flow chart of an exemplary method for generating initial biometric signatures. The method of FIG. 3 provides more detail for step 210 of the method of FIG. 2. A subject is monitored for initial ECG biometric data at step 310. The ECG biometric data may be obtained from a biometric monitor 100 (or 160) configured to monitor the subject, such as an ECG monitor. Initial biometric data is received from the ECG monitor at step 320. The initial biometric data may include enough data to generate an identifying signature or pattern for the monitored subject. At step 330, an initial ECG biometric signature is generated for the subject from the initial ECG biometric data received at step 320. A biometric signature may be generated by manipulating biometric data, processing the data, encoding the data, identifying patterns in the data, and by other processing. For example, when the biometric data is ECG data, the biometric signature may include identification of a pattern in the ECG signal data points.

The subject is monitored for initial pulse oximetry biometric data at step 340. The pulse oximetry biometric data may be obtained from a biometric monitor 100 (or 160) such as a pulse oximetry monitor. Initial biometric data is received from the pulse oximetry monitor at step 350. At step 360, an initial pulse oximetry biometric signature is generated for the subject from the initial pulse oximetry biometric data received at step 350.

As discussed above, more than one type of biometric signature may be generated for a subject. The two or more signatures may be collected simultaneously or separately, but preferably during the same session. Other types of biometric signatures maybe generated for a subject in addition to those discussed with respect to the method of FIG. 3.

Figure 4:
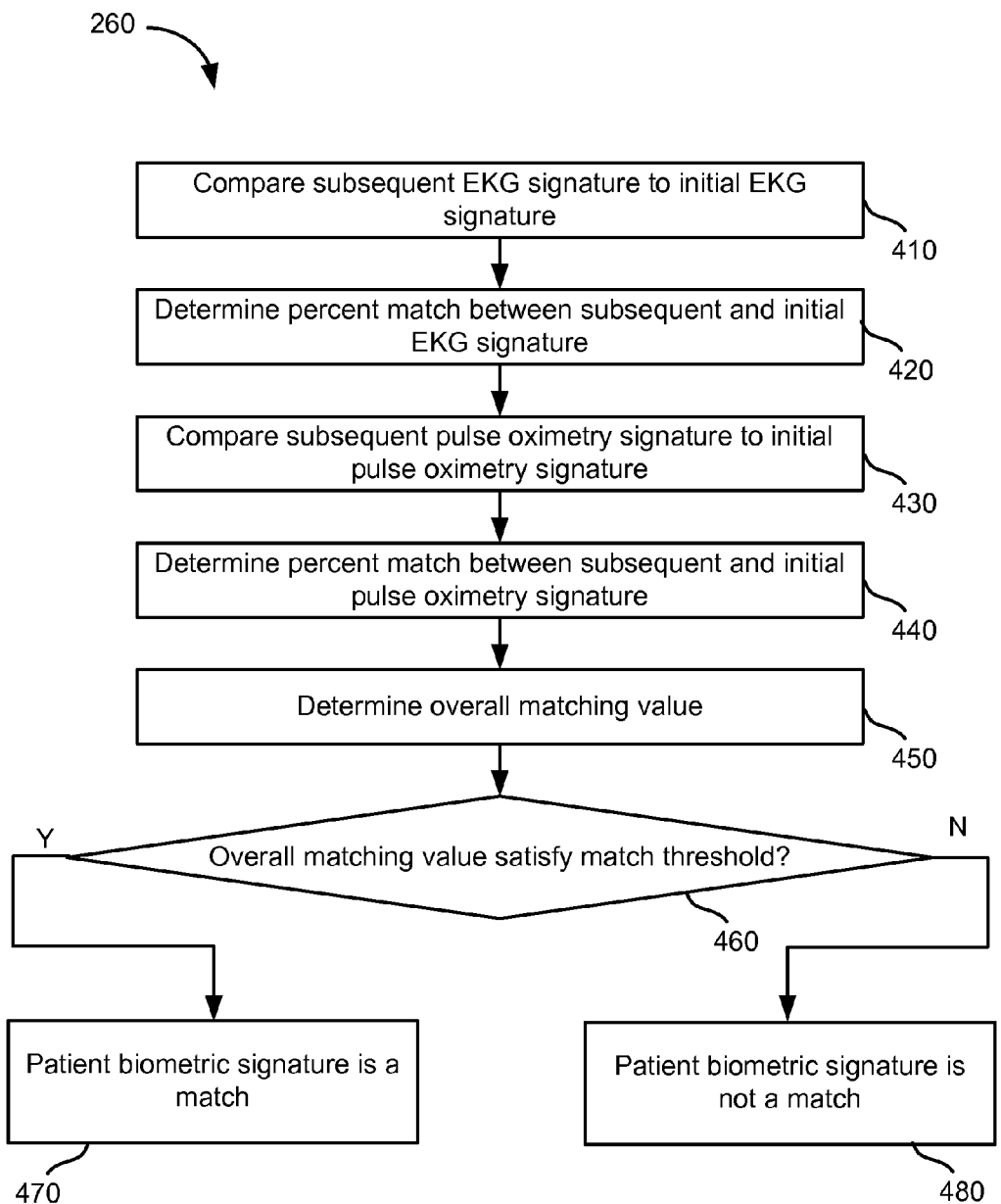
FIG. 4 is a flow chart of an exemplary method for determining a match between biometric signatures.

FIG. 4 is a flow chart of an exemplary method for determining a match between biometric signatures. The method of FIG. 4 provides more detail for step 260 of the method of FIG. 2. A subsequent ECG signature is compared to an initial ECG signature at step 410. A determination is made as to the percent match between the subsequent and initial ECG signature at step 420. The comparison may indicate whether portions of the ECG, for example the electrical patterns detected from different leads, are similar or not within a specified tolerance, such as 5% or 10%. Additionally, in some embodiments, the comparison may determine how many of the features of the initial and subsequent ECG signatures match, such as 90%, 80% or some other portion of the features. The match between the initial and subsequent signatures may be compared using a threshold other than percent match, such as for example a ratio.

A subsequent pulse oximetry signature is compared to an initial pulse oximetry signature at step 430. A determination is made as to the percent match between the subsequent and initial pulse oximetry signature at step 440. The percent match may be between the oxygen levels in the blood, within a threshold matching range of 5% or 10%.

An overall matching value is determined at step 450. The overall matching value may be determined from the percent match values of the one or more signatures generated for the subject. For example, the overall matching value may be generated as an average percent match, a function of weighted percent matching values, or some other means of calculation.

A determination is made at step 460 as to whether the overall matching value satisfies the match threshold at step 460. The value generated at step 450 may be compared to a threshold value at step 460. The threshold value may be 90%, 95%, or some other value. Alternatively, different thresholds may be applied to each comparison performed, rather than applying a single threshold value to an overall matching value. If the overall (or individual) matching value satisfies the corresponding matching threshold, the subject biometric signature is determined to match the initial biometric signature at step 470. If the overall matching value does not satisfy the corresponding matching threshold, the subject biometric signature is determined to not match the initial biometric signature at step 480.

Figure 5:
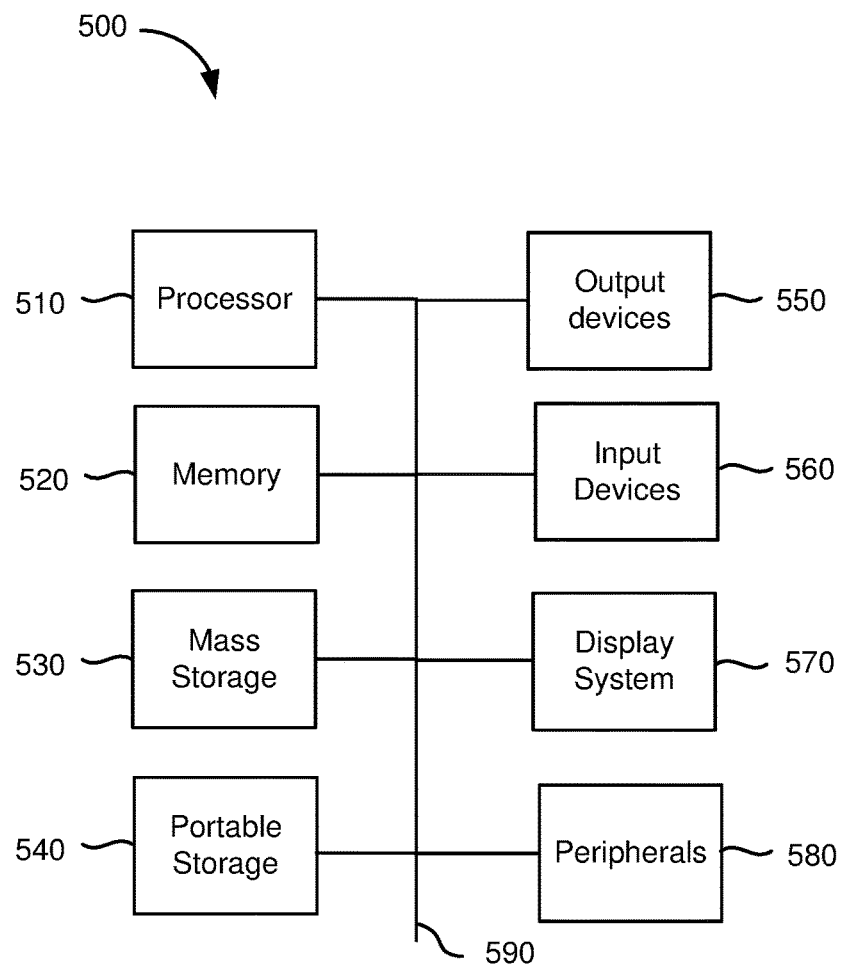
FIG. 5 is a block diagram of an exemplary computing device.

FIG. 5 is a block diagram of an exemplary computing device for gathering and analyzing diagnostic and biometric data in accordance with embodiments of the present invention. In some embodiments, the exemplary computing device of FIG. 5 can be used to implement portions of, Network Server 130, Application Server 120, Work Station 110, Biometric Monitor 100 and 160, and Router/Access Point 150.

The computing system 500 (also referenced as system 500 and computer system 500) of FIG. 5 includes one or more processors 510 and main memory 520. Main memory 520 stores, in part, instructions and data for execution by processor 510. Main memory 520 can store the executable code when in operation. The system 500 of FIG. 5 further includes a mass storage device 530, portable storage device 540, output devices 550, subject input devices 560, a display system 570, and peripheral device(s) 580.

The components shown in FIG. 5 are depicted as being connected via a single bus 590. However, the components can be connected through one or more data transport means. For example, processor 510 and main memory 520 can be connected via a local microprocessor bus, and the mass storage device 530, peripheral device(s) 580, portable storage device 540, and display system 570 can be connected via one or more input/output (I/O) buses.

Mass storage device 530, which can be implemented with a magnetic disk drive or an optical disk drive, is a non-volatile storage device for storing data and instructions for use by processor 510. Mass storage device 530 can store the system software for implementing embodiments of the present invention for purposes of loading that software into main memory 520.

Portable storage device 540 operates in conjunction with a portable non-volatile storage medium, such as a floppy disk, compact disk or Digital video disc, to input and output data and code to and from the computer system 500 of FIG. 5. The system software for implementing embodiments of the present invention can be stored on such a portable medium and input to the computer system 500 via the portable storage device 540.

Input devices 560 provide a portion of a subject interface. Input devices 560 may include an alpha-numeric keypad, such as a keyboard, for inputting alpha-numeric and other information, or a pointing device, such as a mouse, a trackball, stylus, or cursor direction keys. Additionally, the system 500 as shown in FIG. 5 includes output devices 550. Examples of suitable output devices include speakers, printers, network interfaces, and monitors.

Display system 570 may include a CRT, a liquid crystal display (LCD) or other suitable display device. Display system 570 receives textual and graphical information, and processes the information for output to the display device.

Peripheral device(s) 580 may include any type of computer support device to add additional functionality to the computer system. For example, peripheral device(s) 580 may include a modem or a router.

The components contained in the computer system 500 of FIG. 5 are those typically found in computer systems that can be suitable for use with embodiments of the present invention and are intended to represent a broad category of such computer components that are well known in the art. Thus, the computer system 500 of FIG. 5 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

The above-described modules can be comprised of software or instructions that are stored on storage media. The instructions can be retrieved and executed by the processor 510. Some examples of instructions include software, program code, and firmware. Some examples of storage media comprise memory devices and integrated circuits. The instructions are operational when executed by the processor 510 to direct the processor 510 to operate in accordance with embodiments of the present invention. Those skilled in the art are familiar with instructions, processor(s), and storage media.

The present technology is described above with reference to exemplary embodiments. It will be apparent to those skilled in the art that various modifications may be made and other embodiments can be used without departing from the broader scope of the present technology. Therefore, these and other variations upon the exemplary embodiments are intended to be covered by the present technology.

The invention claimed is:

1. A method for determining if an ambulatory sleep monitoring device was used by someone other than a proper subject, the method comprising:
   receiving biometric data from the proper subject's attended diagnostic session;
   generating a first biometric signature specific to the proper subject from the received biometric data from the proper subject's attended diagnostic session;
   receiving sleep apnea data from a subsequent unattended diagnostic session, the sleep apnea data received from an ambulatory sleep monitoring device;
   generating a second biometric signature from the received sleep apnea data from the subsequent unattended diagnostic session;

determining if the second biometric signature matches the first biometric signature;

determining the ambulatory sleep monitoring device was used by someone other than the proper subject if the second biometric signature does not match the first biometric signature and invalidating or terminating the analysis of the sleep apnea data; and determining the ambulatory sleep monitoring device was used by the proper subject if the second biometric signature matches the first biometric signature and validating or continuing the analysis of the sleep apnea data to determine if the proper subject has sleep apnea.

2. The method of claim 1, further comprising generating an initial biometric signature by a computing device from initial biometric data received from a biometric monitor.

3. The method of claim 1, wherein the biometric data and the sleep apnea data include ECG data or pulse-oximetry data or both.

4. The method of claim 3, wherein the sleep apnea data from the subsequent unattended diagnostic session is validated if the ECG data and the pulse-oximetry data are within matching thresholds from an initial ECG biometric signature and an initial pulse-oximetry biometric signature.

5. The method of claim 1, wherein the biometric data for the first biometric signature is collected from the proper subject at a health monitoring facility.

6. The method of claim 1, wherein validating the signature includes confirming the integrity of a valid identification device associated with the proper subject.

7. A non-transitory computer readable storage medium having embodied thereon a program, the program being executable by a processor to perform a method for determining if an ambulatory sleep monitoring device was used by someone other than a proper subject, the method comprising:

receiving biometric data from the proper subject's attended diagnostic session;

generating a first biometric signature specific to the proper subject from the received biometric data from the proper subject's attended diagnostic session;

receiving sleep apnea data from a subsequent unattended diagnostic session, the sleep apnea data received from an ambulatory sleep monitoring device;

generating a second biometric signature from the received sleep apnea data from the subsequent unattended diagnostic session;

determining if the second biometric signature matches the first biometric signature;

determining the ambulatory sleep monitoring device was used by someone other than the proper subject if the second biometric signature does not match the first biometric signature and invalidating or terminating the analysis of the sleep apnea data; and determining the ambulatory sleep monitoring device was used by the proper subject if the second biometric signature matches the first biometric signature and validating or continuing the analysis of the sleep apnea data to determine if the proper subject has sleep apnea.

8. The non-transitory computer readable storage medium of claim 7, wherein diagnostic data is received from a Holter monitor.

9. The non-transitory computer readable storage medium of claim 7, wherein the biometric data and the sleep apnea data include ECG data or pulse-oximetry data or both.

10. The non-transitory computer readable storage medium of claim 9, wherein the sleep apnea data from the subsequent unattended diagnostic session is validated if the ECG data and the pulse-oximetry data are within matching thresholds from an initial ECG biometric signature and an initial pulse-oximetry biometric signature.

11. The non-transitory computer readable storage medium of claim 7, wherein the biometric data for the first biometric signature is collected from the proper subject at a health monitoring facility.

12. A system for determining if an ambulatory sleep monitoring device was used by someone other than a proper subject, the system comprising:

a communications module stored in memory and executed by a processor to receive biometric data from the proper subject's attended diagnostic session;

a signature generation module stored in memory and executed by a processor to generate a first biometric signature specific to the proper subject from the received biometric data from the proper subject's attended diagnostic session;

the communications module further configured to receive sleep apnea data from a subsequent unattended diagnostic session, the sleep apnea data received from an ambulatory sleep monitoring device;

the signature generation module further configured to generate a second biometric signature from the received sleep apnea data from the subsequent unattended diagnostic session;

a signature comparison module stored in memory and executed by a processor to:

determine if the second biometric signature matches the first biometric signature;

determine the ambulatory sleep monitoring device was used by someone other than the proper subject if the second biometric signature does not match the first biometric signature and invalidating or terminating the analysis of the sleep apnea data; and determine the ambulatory sleep monitoring device was used by the proper subject if the second biometric signature matches the first biometric signature and validating or continuing the analysis of the sleep apnea data to determine if the proper subject has sleep apnea.

13. The system of claim 12, wherein the biometric data and the sleep apnea data include ECG data or pulse-oximetry data or both.

* * * * *